US009651557B2

(12) United States Patent
Jehuda-Cohen

(10) Patent No.: US 9,651,557 B2
(45) Date of Patent: May 16, 2017

(54) METHOD AND KIT FOR THE DETECTION OF HEPATITIS-SPECIFIC ANTIBODIES

(71) Applicants: Dror Atzmon, Tel Aviv (IL); Dobroslav Melamed, Rishon Lezion (IL)

(72) Inventor: Tamar Jehuda-Cohen, Moshav Gimzo (IL)

(73) Assignees: Dror Atzmon, Tel Aviv (IL); Dobroslav Melamed, Rishon Lezion (IL)

( * ) Notice: Subject to any disclaimer, the term of this patent is extended or adjusted under 35 U.S.C. 154(b) by 0 days.

(21) Appl. No.: 14/383,574

(22) PCT Filed: Mar. 7, 2013

(86) PCT No.: PCT/IL2013/050217
§ 371 (c)(1),
(2) Date: Sep. 8, 2014

(87) PCT Pub. No.: WO2013/132502
PCT Pub. Date: Sep. 12, 2013

(65) Prior Publication Data
US 2015/0111767 A1    Apr. 23, 2015

Related U.S. Application Data

(60) Provisional application No. 61/608,120, filed on Mar. 8, 2012.

(51) Int. Cl.
*G01N 33/53* (2006.01)
*A61K 39/29* (2006.01)
*G01N 33/576* (2006.01)

(52) U.S. Cl.
CPC ................. *G01N 33/576* (2013.01)

(58) Field of Classification Search
None
See application file for complete search history.

(56) References Cited

U.S. PATENT DOCUMENTS

| 6,264,619 B1* | 7/2001 | Ferguson | A61B 5/1405 206/569 |
| 6,352,826 B1* | 3/2002 | Jehuda-Cohen | G01N 33/569 422/547 |
| 2002/0006608 A1* | 1/2002 | Cohen | G01N 33/569 435/5 |

FOREIGN PATENT DOCUMENTS

WO      2012032512 A2      3/2012

OTHER PUBLICATIONS

Corning, Medium 199, Mar. 2012, 2 pages, available from http://cellgro.com/media/docs/files/items/file_112.pdf.*
Yan et al., International Immunology, 2005, 17(7):869-877.*
Gorodin et al., (2013) New Tools in HCV Diagnosis, in Light of the Enhanced Awareness and the New Drugs for Treatment: SMARTube and Stimmunology. The Scientific World Journal 2013: 389780; 12 pages.
Mumo et al., (2009) Detecting Seronegative-Early HIV Infections Among Adult Versus Student Kenyan Blood Donors, by Using Stimmunology. Exp Biol Med (Maywood) 234(8): 931-939.
Jehuda-Cohen (2011) Window Period Detection of HCV Antibodies by in-vitro Lymphocyte Stimulation. Presented at the CDC-HCV-2011 Symposium: Identification, Screening and Surveillance of HCV Infections in the Era of Improved Therapy for Hepatitis C. 24 pages.    https://www.cdc.gov/hepatitis/resources/mtgsconf/hcvsymposium2011-pdfs/15_jehuda.pdf. Dec. 2, 2011 (Dec. 2, 2011).

* cited by examiner

*Primary Examiner* — Stacy B Chen
(74) *Attorney, Agent, or Firm* — Vorys, Sater, Seymour & Pease LLP

(57) ABSTRACT

The present invention relates to an improved method for detecting antibodies to a hepatitis virus in a tissue sample from individuals, which can reliably detect antibodies in recently infected individuals and which provides much lower false positive results in individuals that have cleared their hepatitis infections. More particularly, the present invention relates to an improved method and kit which utilizes an activator of (i) hepatitis virus-primed lymphocytes, (ii) memory cells specific for said hepatitis virus, (iii) hepatitis virus-specific antibody production, or (iv) a combination thereof in a tissue sample to stimulate the production of antibodies from newly primed B cells, if present.

18 Claims, 3 Drawing Sheets

P=Plasma; SP=SMARTplasma

METHOD AND KIT FOR THE DETECTION OF HEPATITIS-SPECIFIC ANTIBODIES

FIELD OF THE INVENTION

The present invention relates to an improved method for detecting antibodies to a hepatitis virus in a tissue sample from individuals, which can reliably detect antibodies in recently infected individuals, provides much lower false positive results, and differentiates between individuals who are chronically infected with the hepatitis virus and those who have cleared their hepatitis infection. More particularly, the present invention relates to an improved method and kit which utilizes an activator of (i) hepatitis virus-primed lymphocytes, (ii) memory cells specific for said hepatitis virus, (iii) hepatitis virus-specific antibody production, or (iv) a combination thereof in a tissue sample to stimulate the production of antibodies from newly primed B cells, if present.

BACKGROUND OF THE INVENTION

The HCV epidemic is not a new one, yet it has been ignored for some time, while HIV has been the epidemic dealt with on a global and national levels. This silent epidemic, which kills more people than AIDS, is now rising to the public awareness. This is due to several factors such as the HIV-HCV co infection, HCV spreading among HIV positive people and other at risk populations, and the recent emergence of new drugs for treating HCV. These drugs, and hopefully others in the pipeline, have lower toxicity and a shorter duration of treatment—thus making the argument for early treatment stronger, offering a potential for not only curtailing the epidemic, but also to eradicate it. We have gained much insight into the combat of blood born disease while working with HIV, and the lessons learnt there should be applied to HCV, such as the Test & Treat program and the efforts to identify all carriers of the infection.

However, the HCV epidemic presents us with new and different challenges regarding diagnosis, and this in its turn affects treatment decisions:

1. A long seronegative window period—unlike most infections, antibodies against HCV do not appear within 7-10 days of the infection. There is a seronegative window period of several months and thus a negative antibody test does not provide a confirmed, negative, diagnosis. Since the virus resides mainly in the liver, its absence from the blood, at detectable levels also does not constitute a clean bill of health. In individuals with some general immune suppression (e.g. pregnant women, MSM, hemodialysis patients), the window period is even longer. The current antibody tests for HCV antibodies detect only IgG which delays the diagnosis even further. A tool which enables early detection of HCV infection is critical in high risk groups, as seronegative results require repeat testing several weeks or months later, and the return rate for repeat testing is very low. Solving the problem of the long seronegative window period is important for tracking/mapping a potential HCV outbreak. Without early detection tools, the most recent infections are missed, thus giving "delayed" view of the current outbreak and its current scope. This seronegative window period is an immunological enigma as HCV antigens are very immunogenic, and antibodies should have been detectable within days of infection.

2. High (and variable) levels of false positive results—the current HCV diagnostic assays have a relatively high levels of false positives' rate. To add to the complexity of deriving true HCV prevalence information from testing programs and surveys, the false positive rate varies from population to population, and from country to country. This is a major concern as it means, on the epidemiological level that we would be over-estimating prevalence (and in a varying, and unknown, degree) in different population around the world. On another level, the low specificity of the antibody assays affects the blood supply, as it causes a loss of good/safe blood, and the temporary deferral of the donor leads to additional potential loss of blood donations.

The high level of 'noise' in the HCV antibody assays is also a complicating factor in the efforts to develop a diagnostic kit which will detect anti HCV IgM antibodies, efforts which have not been successful to date.

3. The routine antibody testing in serum/plasma does not differentiate between current/chronic infection and cleared/resolved infection. This is important in HCV infection as 15-25% of new HCV infections are spontaneously resolved. Those who resolved the infection still test positive on the antibody assays for many years following the clearance of the virus, as there are very high levels of HCV antibodies in the blood, and IgG has a half-life 21 days. Using molecular assays for the detection of viral genome, offers only a partial solution as the lack of detection of HCV viral genome in measurable levels in the blood is not a clear indication for the state of the infection in the liver. Thus, current assays do not provide a clear diagnosis of current HCV infection.

SUMMARY OF THE INVENTION

In one embodiment, the present invention provides a method for the detection of hepatitis virus-specific antibodies in a sample from a subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby detecting the presence of hepatitis virus-specific antibodies.

In another embodiment, the present invention provides a method for the detection of a hepatitis infection in a subject comprising the steps of (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby detecting a hepatitis infection in said subject.

In another embodiment, the present invention provides a method for the detection of a recent hepatitis infection in a subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby detecting a recent hepatitis infection in said subject.

In another embodiment, the present invention provides a method for detecting a hepatitis infection in a seronegative subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); wherein if the antigen-antibody immune complex is detected, said seronegative subject has a hepatitis infection, thereby detecting a hepatitis infection in said seronegative subject.

In another embodiment, the present invention provides a method of differentiating between a cleared and chronic hepatitis infection in a subject comprising the steps of: (a) obtaining a tissue sample from said subject; (b) determining the anti-hepatitis virus antibody level in a first aliquot of said sample, wherein a detectable anti-hepatitis virus antibody level indicates that a subject is seropositive; (c) stimulating a second aliquot of said sample to produce anti-hepatitis virus antibodies in vitro by incubating said second aliquot in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (d) determining the anti-hepatitis virus antibody level in said second aliquot of said sample; (e) dividing a value representing the stimulated anti-hepatitis virus antibody level obtained in step (d) by a value representing the anti-hepatitis virus antibody level obtained in step (b) for each subject; (f) determining if the quotient obtained in step (d) is above a pre-determined threshold value for each subject, wherein a value below said threshold value indicates that the subject has a cleared hepatitis virus infection and a value close to said threshold value indicates that the subject has a chronic hepatitis infection, thereby differentiating between a cleared and chronic hepatitis infection in said subject.

In another embodiment, the present invention provides a kit for the detection of hepatitis virus-specific antibodies in a subject comprising: a container for retaining a whole blood sample, wherein said container comprises a medium, said medium comprising an activator of (i) lymphocytes activated by said hepatitis virus, (ii) memory cells specific for said hepatitis virus, (iii) antibodies against said hepatitis virus, or (iv) a combination thereof. In another embodiment, the kit may additionally comprise a second container lacking said medium for retaining a whole blood sample. In another embodiment, the kit may additionally comprise an assay for the detection of hepatitis viral-specific antibodies. In another embodiment, the kit may additionally comprise instructions for use.

DETAILED DESCRIPTION OF THE PRESENT INVENTION

Figure 1A:
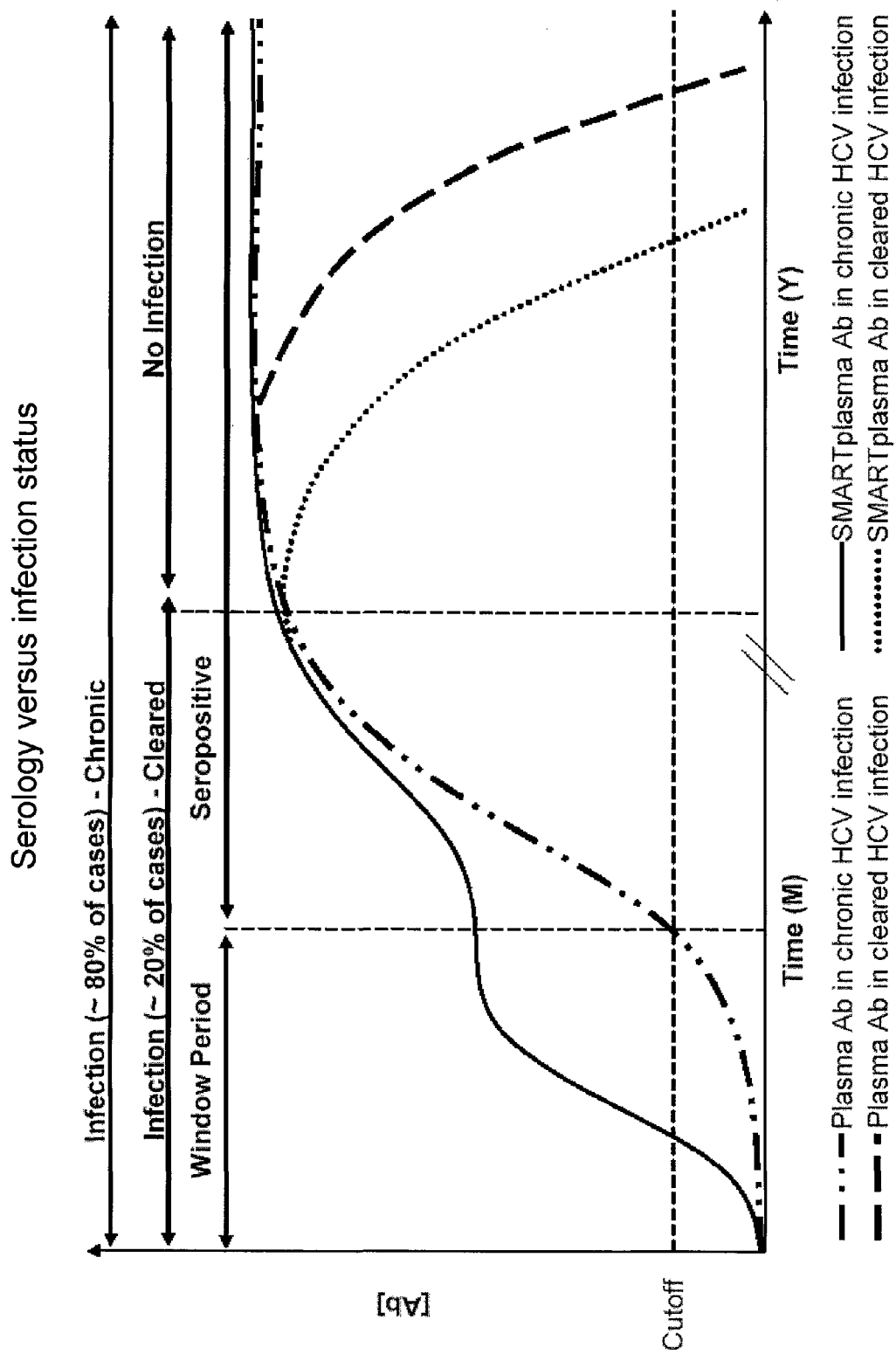
FIG. 1. The Stimulation Index (SI) calculated for blood treated with an activator, over the course of the Hepatitis C Virus (HCV) infection.

In one embodiment, the present invention provides a different approach for improving HCV antibody based diagnosis, so as to meet the challenges stated above. The approach is based on the technology of in vitro stimulating antibody production, i.e. looking not only at the levels of HCV antibodies in the standard plasma sample, but also looking at the levels of HCV antibody produced in-vitro, in a whole blood sample. Measuring not only what had been produced, sometime in the past, but also the current capability and potential for antibody production there is (or is not) at the time of testing.

The technology describes herein enables the production of antibodies, in-vitro, in a whole blood sample, even in the face of peripheral immune suppression. The embodiment of the technology, for the detection and diagnosis of HCV infection can be in the form of one or more activators, a media comprising one or more activators, or a container comprising a media comprising one or more activators or in any form or format of employing the technological concept on a tissue sample. By incubating a small volume of blood (1 ml), in a container as described herein, for several days, antibodies could be produced at detectable levels, even prior to seroconversion. This means that very early infection can be detected, using the currently available diagnostic kits, by using activator-treated plasma (the plasma-supernatant in the container comprising activator, following the incubation of the blood in it) instead of standard plasma, as the sample on the EIA (or any other assay) for HCV diagnosis.

Thus, in one embodiment, by using an activator, media or container as described herein as a blood pre-analytics device, one can overcome the challenge of the long seronegative window period in HCV. The ability to detect very early infection, independently from where the virus is residing at those early stages, and without having to wait for the production of antibodies in-vivo to reach detectable levels, is critical for curtailing the HCV epidemic. A tool which enables early detection of HCV infection could provide an opportunity for early treatment, at stages which might require, in the future, lower doses, and shorter treatment duration (maybe even with mono-therapy).

Clinical-laboratory trials described hereinbelow, in several countries have been conducted, for detecting infected individuals during the seronegative window period. Among blood samples from 2722 high risk individuals, from populations around the world, there were 252 seropositives in regular serology. All those 252 and 13 additional samples were antibody positive, on the same diagnostic kit, after pre-treatment in the container comprising an activator as described herein. Thus, the use of the activator-treated plasma as the sample tested increased diagnostic sensitivity of the assays used, as adding the pre-analytics step to antibody testing, increased HCV detection by 5.2%. It is important to note that these additional positives are at the early stages of infection (the seronegative WP), and thus are the most critical for effective early treatment and for information as to where the epidemic is currently spreading.

In a diagnostic assay, increased diagnostic sensitivity usually comes on the account of reduced specificity, and vise versa. Since the incubation step in the activator-containing container, increases the levels of antibodies in the sample and thus the signal measured/seen in the diagnostic kit, it is necessary to evaluate its effect on the specificity of the HCV diagnostic kits. During testing for HCV in routine use settings, as described herein, 3840 blood samples were tested using both plasma and activator-treated plasma, and there were 27 false positives in plasma. Of these, only one sample was false positive after pre-treatment in a container comprising activators as described herein. Thus, not only no adverse effect on specificity was observed, but rather increased diagnostic specificity was achieved, with a 96% reduction in the false positive rate when using the container comprising activators as described herein. This is probably due to the fact that while the container comprising activators as described herein process increases the levels of the specific HCV antibodies (and thus the 'signal'), it reduces the 'noise' by the dilution of the plasma which occurs in the container comprising activators as described herein (1 ml whole blood, which is approximately 0.5 ml of plasma, put into 2 ml of activator-containing media—a 1:4, or ×5, dilution).

In one embodiment, the ability to drive forward HCV antibody production in a whole blood sample, is dependent on the presence of HCV primed B cells in the blood sample. HCV primed B cells would be present in the blood within days of infection, and newly produced naïve B cells, will be primed by HCV viral antigens for as long as the viral infection will persist. Once the infection is cleared (spontaneously, or following anti-retroviral treatment), there will be no further priming of naïve B cells (or T cells). At that time, while the already produced antibody levels in the blood will remain high for years, the ability to enhance further antibody production, in-vitro, by newly primed B cells, would be gone within days.

The present invention relates to an improved method for detecting antibodies to a hepatitis virus in a tissue sample from individuals, which can reliably detect antibodies in recently infected individuals and which provides much lower false positive results in individuals that have cleared their hepatitis infections. More particularly, the present invention relates to an improved method and kit which utilizes an activator of (i) hepatitis virus-activated lymphocytes, (ii) memory cells specific for said hepatitis virus, (iii) hepatitis virus-specific antibody production, or (iv) a combination thereof in a tissue sample to stimulate the production of antibodies from primed B cells, if present.

In one embodiment, the activator is a lymphocyte primed by hepatitis virus. In one embodiment, the hepatitis virus-primed lymphocytes are activated. In another embodiment, the hepatitis virus-primed lymphocytes are suppressed. In one embodiment, the activator is a lymphocyte activated by hepatitis virus.

In one embodiment, the present invention provides a method for the detection of hepatitis virus-specific antibodies in a sample from a subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby detecting the presence of hepatitis virus-specific antibodies.

In one embodiment, the present invention provides a method of increasing low anti-hepatitis antibody levels in a tissue sample from a subject to a detectable level comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby increasing low anti-hepatitis antibody levels in a tissue sample from said subject to a detectable level.

In another embodiment, the present invention provides a method for the detection of a hepatitis infection in a subject comprising the steps of (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby detecting a hepatitis infection in said subject.

In another embodiment, the present invention provides a method for the detection of an early (recent) hepatitis infection in a subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby providing an early detection of a hepatitis infection in said subject.

In another embodiment, the present invention provides a method of inducing antibody production or expression from HCV primed B cells in a tissue sample from a subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); thereby inducing antibody production or expression from HCV primed B cells in a tissue sample from said subject. In another embodiment, the present invention provides a method of stimulating antibody production from HCV primed B cells in a tissue sample from a subject comprising the steps described hereinabove.

In one embodiment, the primed B cells are activated. In another embodiment, the primed B cells are suppressed.

In another embodiment, the present invention provides a method for detecting a hepatitis infection in a seronegative subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); wherein if the antigen-antibody immune complex is detected, said seronegative subject has a hepatitis infection, thereby detecting a hepatitis infection in said seronegative subject.

In another embodiment, the present invention provides a method for detecting a very recent hepatitis infection in a subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); wherein if the antigen-antibody immune complex is detected, said subject has a very recent hepatitis infection, thereby detecting a very recent hepatitis infection in said subject.

In another embodiment, the present invention provides a method for detecting a hepatitis infection in a subject by raising hepatitis-specific antibody levels comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); wherein if the antigen-antibody immune complex is detected, said subject has a hepatitis infection, thereby detecting a hepatitis infection in said subject by raising hepatitis-specific antibody levels in said subject.

In another embodiment, the present invention provides a method for diagnosing a hepatitis infection in a subject comprising the steps of: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b), wherein if the antigen-antibody immune complex is detected, said subject has a hepatitis infection, thereby diagnosing a hepatitis infection in said subject.

In another embodiment, the present invention provides a method for shortening the window period of a hepatitis infection in a subject, wherein said window period describes a period of time between the time said subject was infection and the time that antibodies to the infectious agent can be reliably detected using a test or assay for the antibody. The steps of the method comprise: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); wherein if the antigen-antibody immune complex is detected, said seronegative subject has a hepatitis infection, thereby shortening the window period of a hepatitis infection in said subject.

In another embodiment, the present invention provides a method for resolving the window period of a hepatitis infection in a subject, wherein said window period describes a period of time between the time said subject was infection and the time that antibodies to the infectious agent can be reliably detected using a test or assay for the antibody. The steps of the method comprise: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); wherein if the antigen-antibody immune complex is detected, said seronegative subject has a hepatitis infection, thereby resolving the window period of a hepatitis infection in said subject.

In another embodiment, the present invention provides a method for closing the window period of a hepatitis infection in a subject, wherein said window period describes a period of time between the time said subject was infection and the time that antibodies to the infectious agent can be reliably detected using a test or assay for the antibody. The steps of the method comprise: (a) incubating a sample from said subject in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (b) exposing the resultant culture of step a) to a hepatitis virus antigen, thereby allowing an antigen-antibody immune complex to form; and (c) detecting the antigen-antibody immune complex of step b); wherein if the antigen-antibody immune complex is detected, said seronegative subject has a hepatitis infection, thereby closing the window period of a hepatitis infection in said subject.

In one embodiment, the window period is shortened by 95%. In another embodiment, the window period is shortened by 90%. In another embodiment, the window period is shortened by 85%. In another embodiment, the window period is shortened by 80%. In another embodiment, the window period is shortened by 75%. In another embodiment, the window period is shortened by 50%. In another embodiment, the window period is shortened by 25%. In one embodiment, shortening of the window period for an infection to under a week is effectively closing the window period.

In another embodiment, the present invention provides a method of differentiating between a cleared and chronic hepatitis infection in a subject comprising the steps of: (a) obtaining a tissue sample from said subject; (b) determining the anti-hepatitis virus antibody level in a first aliquot of said sample, wherein a detectable anti-hepatitis virus antibody level indicates that a subject is seropositive; (c) stimulating a second aliquot of said sample to produce anti-hepatitis virus antibodies in vitro by incubating said second aliquot in a culture in the presence of a medium comprising an activator of (i) hepatitis virus-primed lymphocytes, (ii) memory cells specific for said hepatitis virus, (iii) hepatitis virus-specific antibody production, or (iv) a combination thereof; (d) determining the anti-hepatitis virus antibody level in said second aliquot of said sample; (e) dividing a value representing the stimulated anti-hepatitis virus antibody level obtained in step (d) by a value representing the anti-hepatitis virus antibody level obtained in step (b) for each subject; (f) determining if the quotient obtained in step (d) is above a pre-determined threshold value for each subject, wherein a value below said threshold value indicates that the subject has cleared the hepatitis virus infection and a value close to said threshold value indicates that the subject has a chronic hepatitis infection, thereby differentiating between a cleared and chronic hepatitis infection in said subject.

In one example, the invention includes a container for collecting, retaining, treating, or culturing blood, or a combination thereof. The container can optionally contain a culture medium. The preferred container is a test tube. Other containers such as a vacuum-tube, a bottle, a well (as part of a multi well plate or as a single well/plate) or a flask, containing an effective concentration and formulation of a medium can also be used. The container can be plastic, glass, silicon, synthetic membranes, or metal material (with or without special treatment or coating of the inner or outer surface), or any other material that is compatible with culturing blood. It is to be understood that the present invention also includes blood containing means other then a blood collection tube including, but not limited to, microtiter plates containing wells in which the blood can be incubated, tissue culture flasks, glass flasks such as an erlenmeyer flask, and any other container in which the blood can be cultured.

In one embodiment, the container is a vacuum-tube, which in one embodiment, is a sterile glass or plastic tube with a closure that is evacuated to create a vacuum inside the tube facilitating the draw of a predetermined volume of liquid into the tube.

A container apparatus may include a mechanism for incubating a whole blood sample in a culture, in the absence of $CO_2$ enrichment. The container can be made of a polymer non-toxic to cells in said culture, for example, but are not limited to a polystyrene polymer and a polypropylene polymer. In one embodiment, the container is capable of keeping liquid and vacuum inside said culture container stable. In one embodiment, "capable" describes the ability of the container to maintain a vacuum or to prevent the exit of liquids from the container, when the container is used in a certain way that is specified in the instructions, for e.g. when the top of the container is in a particular position. In another embodiment, the container stably maintains liquid and vacuum inside said culture container.

In another embodiment, the container has a cap, stopper, or lid that has a plurality of positioning mechanisms. In one example, the cap, stopper, or lid has a first and second positioning mechanisms, wherein the first positioning mechanism is capable of being fully closed that facilitates keeping the vacuum inside the container and the second positioning mechanism is capable of providing ventilation and sterile environment, inside the container.

In accordance with the present invention, a blood sample is drawn into a container. The blood sample to be tested is cultured in vitro in the presence of the medium discussed herein. Before and after incubation, an aliquot is taken from the top of the fluid and is then assayed for the presence of desired antibodies using standard ELISA procedures and/or Western Blot analysis and/or any other antibody detection system, which in one embodiment is a Rapid, Chemiluminescence, Luminescence, or any chip (or Bio-chip) system. If the sample is to be assayed at a later date, the supernatant fluid may be collected, frozen and stored. Results may be further evaluated utilizing the technique of polymerase chain reaction (PCR).

In some embodiments, the method further comprises the steps of: (i) collecting a first assay sample prior to the incubation; (ii) measuring the level of antibodies in said first assay sample; (iii) collecting a second assay sample after the incubation; (iv) measuring the level of antibodies in said second assay sample; and (v) comparing the measurements of the levels of antibodies between said first and second assay samples.

In other embodiments, the method further comprises the steps of: (i) collecting a first assay sample prior to the incubation step and storing said first assay sample; (ii) collecting a second assay sample after said incubation step; (iii) measuring the level of antibodies in said first and said second assay sample concurrently; and (iv) comparing the measurements of the levels of antibodies between said first and second assay samples.

In one embodiment, "concurrently" refers to running the first assay sample and second assay sample in the same antibody detecting assay on the same day, which, in one embodiment, provides more direct comparative data and provides less assay variation than assays run on separate days. In one embodiment, the first assay sample is stored until after the incubation and collection of the second sample. In one embodiment, the two samples (i.e. before and after incubating with the activator described herein) are taken from the same tube. In one embodiment, the first sample is from time 0 days and the second sample is from time Xdays, wherein X is the number of days that the sample is incubated with the activator or activators as described herein.

In one embodiment, the present invention provides a tissue sample from a subject for evaluation. In one embodiment, the tissue sample is a blood sample. In another embodiment, the tissue sample is a whole blood sample. In another embodiment, the sample comprises cells in blood or saliva from said subject. In another embodiment, the tissue sample is a cheek or tongue swab. In another embodiment, the tissue sample is a biopsy (e.g. lymph node, liver, etc).

In one embodiment, the medium used in the methods and composition of the present invention comprise a non-carbon dioxide-dependent buffering agent.

In one embodiment, the incubation of the blood in the medium comprising activator and, optionally, a non-carbon dioxide-dependent buffering agent is 2 days. In another embodiment, the incubation is 3 days. In another embodiment, the incubation is 4 days. In another embodiment, the incubation is 5 days. In another embodiment, the incubation is 6 days. In another embodiment, the incubation is 7 days. In another embodiment, the incubation is 3-5 days. In another embodiment, the incubation is 4-7 days.

Culture medium may refer to any medium that can be used to practice the present invention, including but not limited to RPMI 1640, preferably supplemented with appropriate antibiotics and glutamine. Other culture media which may be used in practicing the present invention include, but are not limited to, Eagles, Dulbecco's, McCoy's, Media 199, media for serum-free culture, and Waymouth's media.

In one embodiment, the medium comprises a non-carbon dioxide-dependent buffering agent. In one embodiment, such as medium is buffered by its complement of salts, free base amino acids and galactose substituted for glucose to help maintain physiological pH. In one embodiment, examples of buffering agents include, but are not limited to, HEPES ((4-(2-hydroxyethyl)-1-piperazineethanesulfonic acid) and a phosphate-based buffering agent. In one embodiment, the phosphate-based buffering agent is L15 Medium (Leibovitz).

In one embodiment, the medium comprising a non-carbon dioxide-dependent buffering agent allows incubation of the sample from the subject without the need for a $CO_2$ incubator. Until now, the incubation step with activator required a $CO_2$ incubator with 5% $CO_2$, and the buffering of the media comprised carbonates. The $CO_2$ incubator requires a $CO_2$ tank, which needs to be replenished on a regular basis, and might be considered a hazard due to the pressurized gas. A major advantage of the new formulation and container as described herein is that the buffer has other (or additional) components, so that it maintains an environment which supports complex human tissue culture processes (such as proliferation and differentiation, and high levels of protein secretion), without the enriched 5% $CO_2$ environment.

In one embodiment, an "activator" for use in the compositions and methods of the present invention is a substance that induces the activation of primed B-cells and/or primed T-cells. In another embodiment an activator induces the activation of memory cells. In another embodiment, an activator induces the activation of hepatitis-specific lymphocytes. In one embodiment, an activator induces hepatitis-specific antibody production. In another embodiment, an activator induces hepatitis-specific antibody expression. In one embodiment, hepatitis-specific antibody expression describes expression on the cell membrane. In another embodiment, hepatitis-specific antibody expression describes expression on the cell surface. In another embodiment, an activator induces hepatitis-specific antibody secretion. In another embodiment, an activator induces hepatitis-specific antibody production and expression. In another embodiment, an activator induces hepatitis-specific antibody production, expression, and secretion.

In another embodiment, an activator induces hepatitis-specific antibody expression and secretion. In another embodiment, an activator does a combination of the above. In one embodiment, the substance or activator is a protein or a mixture of proteins, while in another embodiment, the substance or activator is a peptide, a nucleic acid molecule, a chain of nucleotides, a glycoprotein, a carbohydrate molecule, or a combination thereof. In another embodiment, the substance is a mixture of peptides, nucleic acid molecules, glycoproteins, carbohydrate molecules, or a combination thereof. In one embodiment, the nucleic acid molecule is a DNA sequence, and, in another embodiment, the nucleic acid molecule is a cDNA sequence. In another embodiment, the nucleic acid molecule is an RNA sequence, which in one embodiment, is an mRNA sequence. In one embodiment, the nucleic acid molecule comprises a short nucleic acid sequence, which in one embodiment is 1-50 nucleotides, in another embodiment, 1-20 nucleotides, and, in another embodiment, 1-10 nucleotides. In one embodiment, "activation" of cells comprises inducing proliferation of cells, differentiation of cells, enhancement of cellular activity, antibody production and antibody secretion, secretion of various lymphokines and/or cytokines, or a combination thereof.

In one embodiment, the activator is a mitogen. In one embodiment, a "mitogen" is a chemical substance, or a mixture of substances, in one embodiment, a protein, that encourages a cell to commence cell division, triggering mitosis. In one embodiment, a mitogen triggers signal transduction pathways in which mitogen-activated protein kinase is involved, leading to mitosis. In one embodiment, mitogens of the present invention are used to induce mitosis and/or activation in memory B cells. In one embodiment, mitogens of the present invention are used to induce the formation of plasma cells from primed, yet "silenced" or "tolerized", or suppressed, B-cells, and/or from primed differentiating B cells and/or memory B cells.

In one embodiment, the activator of the compositions and methods of the present invention induces the activation of memory cells and/or in-vivo primed B cells specific for the virus of interest. In one embodiment, the activator of the compositions and methods of the present invention induces the activation of memory cells and/or in-vivo primed T cells. In one embodiment, the activator of the compositions and methods of the present invention induces the activation of memory cells and/or in-vivo primed B and T cells.

In another embodiment, the mitogen of the present invention induces the expression of viral-specific antibodies. In another embodiment, the mitogen of the present invention induces the transfer from memory cells and/or in-vivo primed B cells to plasma cells.

In one embodiment, viral antigens are used in conjunction with mitogens to induce activation of memory B cells and/or in-vivo primed B cells. Thus, in one embodiment, the compositions of the present invention, including those for use in the methods of the present invention, additionally comprise an antigen that is specific to the virus of interest which, in one embodiment, aids or enhances the transfer from memory cells, and/or in-vivo primed B cells, to plasma cells. Similarly, the methods of the present invention may comprise incubating a blood sample in a medium comprising a mitogen and a viral antigen.

In one embodiment, an antigen is a compound, composition, or substance that can stimulate the production of antibodies or a T cell response in a subject or an in vitro assay. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. An epitope typically includes at least 3, and more usually, at least 5, about 9, or about 8-10 amino acids in a unique spatial conformation.

In one embodiment, said antigen is added to said culture to shorten the incubation time and to provide diagnosis in situ. In another embodiment, the antigen-antibody immune complex is detected on a solid phase support or carrier, which in one embodiment, is a nitrocellulose strip, a set of labeled or colored beads, or any other carrier. In one embodiment, the carrier may comprise beads with different densities, sizes, labels, colors, fluorescence, as is known in the art.

In one embodiment, the methods of the present invention identify a viral infection. According to this aspect and in one embodiment, the antigen used in the methods and kits of the present invention is a viral surface antigen or a viral core antigen.

In one embodiment, a hepatitis-specific antigen (or several antigens) is used in the compositions and methods of the present invention. In one embodiment, a hepatitis-specific antigen is an immunogenic peptide, which in one embodiment, is a peptide which comprises an allele-specific motif or other sequence such that the peptide will bind an MHC molecule and induce a cytotoxic T lymphocyte ("CTL") response, or a B cell response (e.g. antibody production or memory B cell proliferation) specific to the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein.

In one related aspect, the mitogen used in the invention provided herein can be either T-cell dependent or T-cell independent. In one embodiment, the mitogen used in the compositions and methods of the present invention acts on T-cells, B-cells, or both T cells and B cells. In one related aspect, the mitogen used to induce activation of memory B cells, and/or in-vivo primed B cells, and the expression of virus-specific antibodies is pokeweed mitogen, which in one embodiment, stimulates both B- and T-cells. Other mitogens can be used in practicing the present invention and include, but are not limited to, lectins, such as, concanavalin A, which in one embodiment acts on T cells; bacterial endotoxins, which in one embodiment, is lipopolysaccharide (LPS), which in one embodiment, acts on B cells. In another embodiment, the mitogen is phytohaemagglutinin (PHA), which in one embodiment, acts on T cells. In another embodiment, the mitogen is leucoagglutinin (PHA-L), while in another embodiment, the mitogen is *Pisum sativum* agglutinin (PSA).

In another embodiment, the activator used in the composition and methods of the present invention is a cytokine, or a mixture of cytokines, which in one embodiment is a signaling molecule secreted by specific cells of the immune system and glial cells. In one embodiment, said cytokine is an interleukin or interferon. In one embodiment, the cytokine is a lymphokine. In one embodiment, said lymphokine is Interleukin 1, Interleukin 2, Interleukin 3, Interleukin 4, Interleukin 5, Interleukin 6, Interleukin 10, Interleukin 12, Granulocyte-macrophage colony-stimulating factor, Interferon-gamma, or a combination thereof.

In one embodiment, the cytokine is a mediator of adaptive immunity. In another embodiment, the cytokine is a mediator of natural immunity. In another embodiment, the cytokine is tumor necrosis factor (TNF)-α, a type I interferon (IFN) (which, in one embodiment, is IFN-α or IFN-β), or a chemokine. In another embodiment, the cytokine is transforming growth factor (TGF)-β. In another embodiment, the cytokine is a stimulator of hematopoesis, which in one embodiment, is Granulocyte-Macrophage Colony Stimulating Factor (GM-CSF), Macrophage colony-stimulating factor (M-CSF), or Granulocyte colony-stimulating facto (G-CSF). In another embodiment, the cytokine is Interleukin-17.

In another embodiment, the activator used in the compositions and methods of the present invention is a bacterially derived lipid A, a viral-derived peptide, a virus, a biological agent, an anti-immunoglobulin reagent, an antibody against a B-lymphocyte and/or T-lymphocyte cellular domain, or a combination thereof.

In one embodiment, lipid A is a lipid component of an endotoxin held responsible for toxicity of Gram-negative bacteria and a very potent stimulant of the immune system, in one embodiment, activating monocytes or macrophages. In one embodiment, the lipid A has 6 acyl chains. In one embodiment, lipid A is from group of Gram-negative bacteria, including *Escherichia coli* (*E. coli*), *Salmonella*, *Shigella*, other Enterobacteriaceae, *Pseudomonas, Moraxella, Helicobacter, Stenotrophomonas, Bdellovibrio*, acetic acid bacteria, *Legionella*, cyanobacteria, spirochaetes, green sulfur or green non-sulfur bacteria.

In one embodiment, the activator used in the compositions and methods of the present invention is a lectin. In one embodiment, the lectin is a Mannose binding lectin, which in one embodiment, is Concanavalin A, Lentil lectin, or Snowdrop lectin. In another embodiment, the lectin is a Galactose/N-acetylgalactosamine binding lectin, which in one embodiment, is Ricin, *Ricinus communis* Agglutinin, RCA120; Peanut agglutinin; Jacalin; or Hairy vetch lectin. In another embodiment, the lectin is a N-acetylglucosamine binding lectin, which in one embodiment, is Wheat Germ agglutinin. In another embodiment, the lectin is a N-acetylneuraminic acid binding lectin, which in one embodiment, is Elderberry lectin, *Maackia amurensis* leukoagglutinin, or *Maackia amurensis* hemoagglutinin. In another embodiment, the lectin is a Fucose binding lectin, which in one embodiment is Ulex *europaeus* agglutinin and, in another embodiment, *Aleuria aurantia* lectin.

In another embodiment, a commercially available container comprising activators as described herein comprising an activator is used as the activator in the compositions and methods of the present invention.

The optimal concentration of mitogen or other activator is easily determined without undue experimentation by one of ordinary skill in the art. In one related aspect, the mitogen concentration range used in the methods provided herein is between approximately 1:10 and 1:5000 dilutions of stock concentration. In another aspect, the concentration range is between 1:100 and 1:500 dilutions of stock. In another embodiment, the mitogen is a lectin, a bacterial endotoxin, a virus, a nucleic acid sequence, lipid A or a lymphokine. In another aspect, the mitogen affects memory cells, wherein the memory cells are B-lymphocytes, T-lymphocytes, or both. In another aspect, the mitogen affects antigen-primed cells, wherein the primed cells are B-lymphocytes, T-lymphocytes, or both.

In one embodiment, the compositions of the present invention and the compositions for use in the methods of the present invention comprise a single activator, which in one embodiment is a mitogen, which in one embodiment, is pokeweed mitogen. In another embodiment, the compositions of the present invention and the compositions for use in the methods of the present invention comprise one or more activators. In another embodiment, the compositions of the present invention and the compositions for use in the methods of the present invention comprise two activators, in another embodiment, three activators, in another embodiment, four activators, and, in another embodiment, five or more activators. In the case where more than one activator is included, each activator may be from a different class, or each activator may be from the same class. For example, the composition comprises a mitogen, a lymphokine, and a B-lymphocyte cellular domain antibody, which in one embodiment is pokeweed mitogen, interleukin-6, and anti-IgD antibody, respectively. In another embodiment, the composition comprises two mitogens, which in one embodiment are pokeweed mitogen and lipopolysaccharide. It is to be understood that any combination of activators as described herein are to be considered part of the invention.

In another embodiment, the compositions of the present invention and the compositions for use in the methods of the present invention comprise one or more activators and an antibody against a B-lymphocyte membrane domain.

In one related aspect, stimulation of memory cells, and/or the primed cells, is achieved by using antibodies against cellular membrane domains. In another embodiment, memory cells, and/or the primed cells, are stimulated by using antibodies against a B-lymphocyte cellular domain, which in one embodiment is a B-lymphocyte membrane domain.

In one embodiment, methods and compositions of the present invention comprise anti-IgD, anti-IgG, anti-IgA, anti-IgE, anti-CD19, anti-CD20, anti-CD80, anti-CD86, anti-L25, anti-L22, anti-L23, anti-L24, anti-L27, anti-CD10, anti-CD23, anti-CD25, anti-CD40 antibodies, or a combination thereof. Methods of making these antibodies are well known in the art and the antibodies are commercially available.

In one embodiment, the compositions of the present invention comprise an anti-IgD antibody. In one embodiment, IgD is membrane-expressed by naïve B cells, initially primed B cells, and memory cells. In one embodiment, plasma cells do not express membrane IgD. In one embodiment, primed B cells that have not fully differentiated to plasma cells can be stimulated or activated by contacting them with anti-IgD. IgD is secreted by B cells. In another embodiment, the compositions of the present invention comprise an anti-IgM antibody.

In another embodiment, the B-lymphocyte membrane domain to which an antibody is directed in the context of the compositions including kits and methods of the present invention is a membrane domain, which in one embodiment, is not secreted from the B-lymphocyte. In another embodiment, the B-lymphocyte membrane domain to which an antibody is directed is a non-secreted protein. In another embodiment, the B-lymphocyte membrane domain to which an antibody is directed is not an immunoglobulin. In another embodiment, anti-IgD is excluded as an antibody against a B-lymphocyte membrane domain in the compositions including kits and methods of the present invention. In another embodiment, anti-IgM is excluded as an antibody against a B-lymphocyte membrane domain in the compositions including kits and methods of the present invention.

In one embodiment, an "antibody" is a polypeptide ligand comprising at least a light chain or heavy chain immunoglobulin variable region which specifically recognizes and binds an epitope (e.g., an antigen, such as a tumor or viral antigen or a fragment thereof). This includes intact immunoglobulins and the variants and portions of them well known in the art, such as Fab' fragments, F(ab)'.sub.2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, Pierce Catalog and Handbook, 1994-1995 (Pierce Chemical Co., Rockford, Ill.); Kuby, J., Immunology, 3.sup.rd Ed., W.H. Freeman & Co., New York, 1997.

In one embodiment, the terms "antibody" and "immunoglobulin" are used interchangeably herein. These terms are well understood by those in the field, and refer to a protein consisting of one or more polypeptides that specifically binds an antigen. The basic structural unit of an antibody is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The term "antibody" also includes any protein or peptide-containing molecule that comprises at least a portion of an immunoglobulin molecule, such as, but not limited to, one complementarity determining region (CDR) of a heavy chain or light chain constant region, a framework region, or any portion thereof. Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids) similarly comprise a variable region (of about 116 amino acids) and one of the aforementioned heavy chain constant regions or classes, e.g., gamma (of about 330 amino acids). The subunit structures and three-dimensional configurations of different classes of immunoglobulins are well known.

In one aspect, stimulation of memory cells, and/or primed cells, results in transformation of the memory cell and/or primed cells to an antibody-secreting plasma cell, whereby the plasma cell secretes antigen-specific antibodies.

In one embodiment, a hepatitis virus-activated lymphocyte of the present invention is a B-lymphocyte. In another embodiment, a hepatitis virus-activated lymphocyte of the present invention is a T-lymphocyte. In one embodiment, a hepatitis virus-primed lymphocyte of the present invention is a B-lymphocyte. In another embodiment, a hepatitis virus-primed lymphocyte of the present invention is a T-lymphocyte. In one embodiment, a memory cell of the present invention is a B-lymphocyte. In another embodiment, a memory cell of the present invention is a T-lymphocyte. In a related aspect, the B lymphocyte of the methods provided herein is a memory B-lymphocytic cell. In another related aspect, the T lymphocyte is a memory T-lymphocytic cell. In yet another related aspect, the activator provided herein activates a memory B-lymphocytic cell. In another embodiment, the activator activates a memory T-lymphocytic cell, and in another embodiment the activator activates both T and B cells.

In one embodiment, the initial viral infection results in the priming of naïve B cells and in the generation of primed B lymphocytes specific for a viral antigen that remain dormant and can be reactivated to produce antibody-secreting plasma cells that secrete antigen-specific antibodies. In another related aspect, the antibodies are specific for a viral antigen, protein, peptide, or epitope. In another related aspect, the antigen is a peptide, protein, sugar, component of the virus, etc.

In one embodiment, the medium described hereinabove further comprises a hepatitis-specific antigen, thereby allowing an antigen-antibody immune complex to form. In another embodiment, the medium further comprises a means for detecting an antigen-antibody immune complex.

In one embodiment, the hepatitis infection of the present invention is a very early hepatitis infection. In one embodiment, the hepatitis infection of the present invention is an early hepatitis infection. In another embodiment, the hepatitis infection of the present invention is a recent hepatitis infection. In another embodiment, the hepatitis infection of the present invention is a cleared hepatitis infection. In another embodiment, the hepatitis infection of the present invention is a chronic hepatitis infection.

In another embodiment, the hepatitis infection is a hepatitis A virus (HAV) infection, hepatitis B virus (HBV) infection, hepatitis C virus infection (HCV), hepatitis D virus (HDV) infection, or hepatitis E virus (HEV) infection.

In one embodiment, the hepatitis infection is a hepatitis A virus (HAV) infection, hepatitis B virus (HBV) infection, hepatitis D virus (HDV) infection, or hepatitis E virus (HEV) infection, or a combination thereof, but not a hepatitis C virus infection (HCV).

In one embodiment, the methods and compositions of the present invention involve the detection of hepatitis virus infection and/or antibodies. In one embodiment, the presentation of hepatitis includes swelling and inflammation of the liver. In one embodiment, hepatitis is acute hepatitis. In another embodiment, hepatitis is chronic hepatitis.

In one embodiment, the methods and composition of the present invention are used to diagnose/measure HAV infection. In one embodiment, Hepatitis A (formerly known as infectious hepatitis and epidemical virus) is an acute infectious disease of the liver caused by the hepatitis A virus (Hep A), an RNA virus, usually spread the fecal-oral route; transmitted person-to-person by ingestion of contaminated food or water or through direct contact with an infectious person. Tens of millions of individuals worldwide are estimated to become infected with Hep A each year. In one embodiment, Hep A infections are usually self-limiting. In one embodiment, raised IgM and IgG antibodies to hepatitis A (IgM is usually positive before IgG) are an indication of HAV infection. In another embodiment, elevated liver enzymes (liver function tests), especially transaminase enzyme levels are an indication of HAV infection.

In one embodiment, the methods and composition of the present invention are used to diagnose/measure HBV infection. In one embodiment, Hepatitis B virus is an hepadnavirus—hepa from hepatotropic (attracted to the liver) and dna because it is a DNA virus—and it has a circular genome of partially double-stranded DNA. The viruses replicate through an RNA intermediate form by reverse transcription, which practice relates them to retroviruses. Although replication takes place in the liver, the virus spreads to the blood where viral proteins and antibodies against them are found in infected people. Originally known as "serum hepatitis", the disease has caused epidemics in parts of Asia and Africa, and it is endemic in China. About a third of the world population has been infected at one point in their lives, including 350 million who are chronic carriers.

The virus is transmitted by exposure to infectious blood or body fluids such as semen and vaginal fluids, while viral DNA has been detected in the saliva, tears, and urine of chronic carriers. Perinatal infection is a major route of infection in endemic (mainly developing) countries. Other risk factors for developing HBV infection include working in a healthcare setting, transfusions, and dialysis, acupuncture, tattooing, extended overseas travel and residence in an institution. In one embodiment, the acute illness causes liver inflammation, vomiting, jaundice and, rarely, death. Chronic hepatitis B may eventually cause cirrhosis and liver cancer.

In one embodiment, the following tests are done to help diagnose and monitor people with hepatitis B: Antibody to HBsAg (Anti-HBs)—a positive result means you have either had hepatitis B in the past, or have received a hepatitis B vaccine; Antibody to hepatitis B core antigen (Anti-HBc)—a positive result means you had a recent infection or an infection in the past Hepatitis B surface antigen (HBsAg)—a positive result means you have an active infection; Hepatitis E surface antigen (HBeAg)—a positive result means you have a hepatitis B infection and are more likely to spread the infection to others through sexual contact or sharing needles.

In one embodiment, the present invention provides a method of detecting a break-through HBV infection in a subject or in a sample from a subject. In one embodiment, the present invention provides a method of detecting a HBV re-infection in a subject or in a sample from a subject. Such detection methods are critically needed in blood banks throughout the HBV-immunized world.

In one embodiment, a breakthrough infection as described herein, is an infection that occurred in a subject after vaccination of said subject with a vaccine against the infectious agent. In one embodiment, the vaccination was not a live virus vaccine. In one embodiment, the vaccination was a protein subunit vaccine. In one embodiment, the vaccination was a killed vaccine. In one embodiment, the vaccination was a viral mutant vaccine. In another embodiment, the vaccination was any type known in the art. In another embodiment, a breakthrough infection is an infection caused by the shedding of live virus from a vaccine. In one embodiment, a breakthrough infection is a full-blown infection. In another embodiment, a breakthrough infection is mild. In one embodiment, a breakthrough infection may cause significant or serious illness in a person with a compromised immune system, such as, in one embodiment, a subject infected with hepatitis.

In one embodiment, a re-infection as described herein, is a second or subsequent infection by the same agent as a first infection. In one embodiment, the re-infection is with HCV. In another embodiment, the re-infection is with HBV. In one embodiment, the re-infection is with a mutant strain of the same virus, and in one embodiment, drug-resistant strain of the virus. In one embodiment, an infection is a super-infection.

In one embodiment, the methods and composition of the present invention are used to diagnose/measure HCV infection. In one embodiment, there are at least six genotypes of HCV. It is to be understood that the methods and composition of the present invention may be used to diagnose/measure any of the genotypes of HCV.

HCV infection is often asymptomatic, but chronic infection can lead to scarring of the liver and ultimately to cirrhosis. In some cases, those with cirrhosis will go on to develop liver failure, liver cancer or life-threatening esophageal and gastric varices.

HCV is spread primarily by blood-to-blood contact associated with intravenous drug use, poorly sterilized medical equipment and transfusions. An estimated 130-170 million people worldwide are infected with hepatitis C. Hepatitis C was originally called "non-A non-B hepatitis". The virus persists in the liver in about 85% of those infected. In one embodiment, HCV is detected using an EIA assay to detect hepatitis C antibody and/or Hepatitis C RNA assays to measure virus levels (viral load).

In one embodiment, the methods and composition of the present invention are used to diagnose/measure HDV infection. In one embodiment, HDV is classified as Hepatitis delta virus. In one embodiment, HDV is a small circular enveloped RNA virus. HDV is considered to be a subviral satellite because it can propagate only in the presence of the hepatitis B virus (HBV). Transmission of HDV can occur either via simultaneous infection with HBV (coinfection) or superimposed on chronic hepatitis B or hepatitis B carrier state (superinfection).

Both superinfection and coinfection with HDV results in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B virus, hepatitis D has the highest mortality rate of all the hepatitis infections of 20%.

In one embodiment, the methods and composition of the present invention are used to diagnose/measure HEV infection. HEV is a positive-sense single-stranded RNA icosahedral virus with a 7.5 kilobase genome. HEV has a fecal-oral transmission route.

In one embodiment, Albumin level, Liver function tests, and/or Prothrombin time are used to evaluate liver damage that may accompany hepatitis infection.

In one embodiment, the compositions and methods of the present invention are for detecting antibodies in and for diagnosing subjects with a hepatitis infection, which is, in one embodiment, a hepatitis C infection. In one embodiment, the hepatitis infection is detected in subjects that have not seroconverted, which in one embodiment, is a subject who does not test positive for anti-hepatitis antibodies on a standard assay. In one embodiment, the activators described herein elicit anti-hepatitis antibodies in a blood sample of a subject who is seronegative, which in one embodiment, means that the subject does not have detectable antibodies to an antigen from the hepatitis with which he has been infected. In one embodiment, seronegativity indicates either a lack of infection or an early stage of infection. According to the latter embodiment, the window period is the period of time between infection with a hepatitis virus and creation of measurable antibody levels against the hepatitis virus. For some hepatitis viruses, the window period is a matter of days or weeks, while for others, the window period is a matter of weeks or months. In one embodiment, the window period may vary by individual, and in particular, depending on their immune state.

In another embodiment, the methods of the present invention are for detecting antibodies in and for diagnosing subjects who are seropositive for the hepatitis infection. In another embodiment, the methods of the present invention are for detecting antibodies in and for diagnosing subjects who have undergone seroconversion.

In one related aspect, the present invention provides methods that enable an increase in the levels of the anti-hepatitis antibodies, thus increasing the signal while reducing the noise. In another embodiment, the method of the present invention increases the signal to noise ratio. In another embodiment, the method of the present invention increases the levels of anti-hepatitis antibodies without significantly increasing the noise levels. In another embodiment, the method of the present invention increases the levels of anti-hepatitis antibodies without affecting the diagnosis or diagnostic specificity.

In one embodiment, a complex between a sample hepatitis antibody and a supplied hepatitis antigen can detected through use of a probe directed against a serum antibody. The reaction mixture can be exposed to conditions sufficient for formation of a probe/antibody complex. The presence, absence or quantity of the probe, probe/antibody complex, or probe/antibody/antigen complex can then be detected. The probe can be directed against human immunoglobulin. For example, probes directed against human immunoglobulin include, but are not limited to, an antibody, an antigen-binding fragment thereof, an aptamer or an avimer. Detection of the presence, absence or quantity of a complex between a probe/antibody complex or probe/antibody/antigen complex can be according to any suitable means known in the art, as discussed herein. A probe for use with a sample hepatitis antibody and a supplied hepatitis antigen can include a label. Probe labels and detection thereof are known in the art.

The biological sample collected by the methods provided herein may be brought into contact with, and immobilized onto, a solid phase support or carrier, such as nitrocellulose, polymer "beads", chips, or other solid support or matrix, which is capable of immobilizing cells, cell particles, membranes, or soluble proteins. The support may then be washed with suitable buffers, followed by treatment with the detectably labeled anti-human antibody. The solid phase support may then be washed with buffer a second time to remove unbound antibody. The amount of bound label on the solid support may then be detected by conventional means.

In one embodiment, the container comprising the whole blood and the activators may further comprise a label in non-soluble form bound on a solid support, which in one embodiment, enables the subject to receive a diagnosis after an appropriate period of incubation. Such incubation periods are dependent on the label and on the time required for the activation step. In another embodiment, the label is in soluble form.

In one related aspect, methods of identifying antibodies produced by the methods provided herein through their binding affinities or specificities are very well known in the art and include methods such as immunoprecipitation or an in vitro binding assay, such as radioimmunoassay (RIA) or enzyme-linked immunoabsorbent assay (ELISA). Other well-known methods can be used to determine antibody binding affinities and these methods can be readily used, as will be understood by a skilled artisan. Polymerase chain reaction (PCR) technique may also be used to enhance the detection level of the preliminary incubation sample. It is to be understood that other assays known in the art to obtain or detect antibody interactions can also be used and these include but are not limited to immuno (Western) blots, immunofluorescence assays, and the like. In another embodiment, all types of bio-chips, lab-chips, and microarray assays can be used. It should be understood by one of skill in the art that any number of conventional protein assay formats, particularly immunoassay formats, may be designed to utilize the isolated antigens and antibodies of this invention for the detection of anti-viral antibodies and for the detection of a viral infection in a subject. This invention is thus not limited by the selection of the particular assay format and encompasses assay formats which are known to those of skill in the art.

The method of the present invention includes optionally separating the blood cells from the fluid portion of the blood so that the presence of antibodies, or the presence of antibody-producing cells can be determined. The separation of the blood cells from the fluid portion of the blood can be done by any of several methods well known to those of ordinary skill in the art, including centrifugation, red-cell lysis, or filtration. In one embodiment, the blood cells are not physically separated from the fluid. In another embodiment, peripheral blood mononuclear cells (PBMCs), B-lymphocytes and T-lymphocytes may be separated from the blood prior to culture and assay. Methods of B cell and T cell enrichment are well known in the art and can be carried out by methods that include, but are not limited to, separation by density, cell sorting/FACS. After incubation of the whole blood with the mitogen, fluid from the top of the blood can easily be extracted and tested for antibody. Optionally, the red blood cells can be lysed either by mild osmotic shock or with a mild detergent. In this way, the white blood cells remain viable.

Generally, the results of a test or assay according to the invention can be presented in any of a variety of formats. The results can be presented in a qualitative fashion. For example, the test report may indicate only whether or not a particular virus was detected, perhaps also with an indication of the limits of detection. The results may be presented in a semi-quantitative fashion. For example, various ranges may be defined, and the ranges may be assigned a score (e.g., 1+ to 4+) that provides a certain degree of quantitative information. Such a score may reflect various factors, e.g., the intensity of the signal (which may indicate the level of expression of antibody bearing cells) the levels of the antibodies produced (as a total sum or as a composition of different subset), etc. The results may be presented in a quantitative fashion, e.g., as a percentage of cells in which (or on which) the antibody is detected, as a antibody level or concentration (as determined via antibody and/or antigen binding assay), etc. As will be appreciated by one of ordinary skill in the art, the type of output provided by a test will vary depending upon the technical limitations of the test and the biological significance associated with detection.

In one embodiment of the present invention, whole blood is collected in a blood collection tube containing culture medium and mitogen. The blood samples are then incubated with an optimized final dilution of pokeweed mitogen at varying concentrations of blood or of viable cells per ml for 1-7 days at 37° C. in a 3-8% $CO_2$ humidified atmosphere. The blood (or cell) culture could be centrifuged (but it is not required) and the supernatant fluid is collected and assayed within 1-7 days for reactive antibodies by any technich, including, but not limited to, ELISA and/or immuno-blot (e.g. Western blot, RIBA) techniques. In the alternative, an aliquot of fluid may be taken directly from the sample.

In one embodiment, the methods of the present invention additionally comprise the step of exposing a separate aliquot from a sample from the subject to the hepatitis virus antigen. In one embodiment, if an antigen-antibody immune complex is detected in the stimulated but not the unstimulated aliquot, the subject has a very early hepatitis infection, which in one embodiment, is an infection in the window period, which in one embodiment, is called a window period (WP) infection. In another embodiment, if the level of said antigen-antibody immune complex is higher in step c) than in step d), the subject has a recent hepatitis infection. In another embodiment, if the level of said antigen-antibody immune complex is higher in step d) than in step c), the subject has a cleared hepatitis infection. In another embodiment, if the level of said antigen-antibody immune complex is detectable in step d) but not in step c), the subject has a cleared hepatitis infection.

In one embodiment, a cleared hepatitis infection has been cleared by the subject's immune system. In another embodiment, a hepatitis infection is cleared spontaneously. In another embodiment, the hepatitis infection is cleared following one or more therapeutic courses, or in another embodiment, treatments. In another embodiment, if the levels of the antigen-antibody immune complex are lower in the stimulated versus the unstimulated aliquot, the subject has a resolved hepatitis infection. In another embodiment, if the levels of the antigen-antibody immune complex are lower in the stimulated versus the unstimulated aliquot, the subject has recovered from a hepatitis infection.

In another embodiment, the methods of the present invention additionally comprises the step of exposing a separate aliquot from a sample from the subject to the hepatitis virus antigen, wherein if the level/amount of the antigen-antibody immune complex in the unstimulated and the stimulated aliquot are equivalent, the subject has a chronic and/or long-term hepatitis infection that has not cleared and that is not very early or recent.

In one embodiment, a method of the present invention requires determining the anti-hepatitis antibody level in an aliquot of a blood sample. In one embodiment, an "aliquot" is a portion of the total amount of a blood sample. In one embodiment, the aliquots used in the methods of the present invention are of equal volume or dilution. In one embodiment, duplicate blood samples are used in the methods of the present invention. In one embodiment, the first and second aliquots of a blood sample are portions of a single blood sample drawn from a single subject at a single time point.

In another embodiment, a single aliquot of the tissue or blood sample may be used to determine both "baseline" antibody levels and stimulated antibody levels, wherein a tissue sample, such as blood is drawn into a container comprising the activator described herein and the cells are sedimented (by regular G force, or by a short centrifugations at low speed). A small aliquot of the plasma supernatant is removed for later testing of the initial levels of hepatitis. The rest is incubated with the activator for several days. The level of the antibodies against hepatitis for the aliquot removed at Time0 is measured on the same assay with an aliquot of blood or tissue removed after the incubation. The two measurements are compared. In one embodiment, the delta (in one embodiment, the difference between the two values) is calculated, in another embodiment, the ratio of signals or levels, is calculated, in another embodiment, the ratio of IgM to IgG of antibodies against hepatitis is calculated, etc. In one embodiment, the ratio between the stimulated and unstimulated aliquots is called the Stimulation Index or SI.

In one embodiment, the SI may be used to determine the time since a hepatitis infection, since as can be seen in FIG. 1, there is a larger difference in stimulated vs unstimulated antibody concentration earlier in the infection, both before and after seroconversion, whereas the difference decreases until it disappears as infection progresses until the infection clears, in which case the antibody levels are reversed, now being higher in the unstimulated aliquot and lower in the stimulated aliquot. This behavior of stimulated and unstimulated hepatitis-infected blood may be used to estimate the time since infection.

In addition, the SI or antibody concentration in stimulated versus unstimulated samples may be used to determine the rate of new incidences of hepatitis infection in a population. In one embodiment, the present invention provides a method of determining the incidence of "new" hepatitis infections in a population. In one embodiment, "new" hepatitis infections are understood to be "recent" hepatitis infections. In one embodiment, recent infections are determined based on a pre-determined SI value and Mean Recency Duration value, which in turn are based on analysis of an initial population in which the recency of infection is known, as is understood by one skilled in the art.

In one embodiment, "new" hepatitis infections are understood to be "very early", or window period (WP) hepatitis infections. In one embodiment, very early/WP infections are determined based on a very high (or ∞) SI value and Mean Window-Period Duration value, which in turn are based on analysis of a given population in which the WP of infection is known, as is understood by one of skill in the art.

In one embodiment, the Stimulation Index (SI) value describes the level of anti-hepatitis antibody in a non-activated blood sample versus an activated blood sample. In one embodiment, the SI values will be measured with varying sensitivity or amplitude depending on the detection system used. Thus, the SI values considered as "elevated" in accordance with the present invention will depend upon the precise procedure utilized. The SI values can be tested against samples obtained from individuals known to be recently infected with hepatitis and compared with similar samples obtained from individuals who have an established hepatitis infection such as, but not limited to, individuals who are known to have been infected for at least 1 year or so. Upon comparison of the results, a suitable SI value can be determined which readily distinguishes a recent infection as defined herein from an established/chronic infection. Assay variation can be controlled by using the value from a standard set of sample pairs. A skilled artisan could readily use standard techniques to determine a suitable SI threshold value when using any of a variety of methods of detecting immunoreactivity to a hepatitis antigen. In one embodiment, the methods of the present invention further comprise the step of determining or estimating a threshold SI value, wherein a value within the range of a threshold indicates that the subject was not recently infected and a value above said threshold indicates that the subject was recently infected. In one embodiment, the threshold SI value is the pre-determined threshold used in the methods of the invention.

In one embodiment, the methods of the present invention comprise calculating the mean number of recently infected subjects divided by the number of seropositive subjects, or the number of total tested, and multiplied by the Mean Recency Duration for said threshold. In one embodiment, the methods of the present invention comprise calculating the mean number of recently infected subjects divided by the product of the number of seropositive subjects, or the number of total tested, and the Mean Recency Duration for said threshold. In another embodiment, (the mean number of recently infected subjects/the number of seropositive subjects)× the Mean Recency Duration for the threshold=a measure of the incidence of new viral infections in said population.

In one embodiment, the "Mean Recency Duration" is a pre-determined time period defined as recent for said threshold. In one embodiment, "recency" is described by the "Mean Recency Duration", which in one embodiment, is the average time period after infection in which there is an SI greater than the threshold value described hereinabove. For example and in one embodiment, the Mean Recency Duration may be 1 year for a SI threshold value of 1.2, which would mean that subjects with an SI value of 1.2 or higher were likely infected within the last year. In one embodiment, the methods of the present invention further comprise the step of determining or estimating the Mean Recency Duration for a specific SI threshold.

In one embodiment, the present invention provides a method of determining the incidence of "new" hepatitis infections in a population. In one embodiment, "new" hepatitis infections are understood to be "recent" viral infections. As described hereinabove, recent infections are determined based on a pre-determined SI value and Mean Recency Duration value, which in turn are based on analysis of an initial population in which the recency of infection is known, as is understood by one of skilled in the art.

In accordance with the present invention, a blood sample is drawn into a test tube, which in one embodiment, is a vacuum-tube, a bottle, a well (as part of a multi well plate or as a single well or plate) or a flask, containing an effective concentration of a solution of a activators (such as lectins, mitogens, cytokines, lymphokines, and combinations thereof as described hereinabove). The blood sample to be tested is cultured in vitro in the presence of any combination of activators of lymphocytes to achieve the same function.

In one embodiment, the step of determining anti-hepatitis antibody levels comprises performing an antibody assay on each aliquot of said blood samples. In one embodiment, an antibody assay comprises exposing each of said blood samples to a viral antigen thereby allowing an antigen-antibody immune complex to form and detecting said antigen-antibody immune complex. In one embodiment, detection of the antigen-antibody immune complex is semi-quantitative.

In one embodiment, a sample of the present invention is obtained from a bodily fluid, such as fresh whole blood in which a single aliquot is activated and the rest of the sample is not activated, as described herein, or in another embodiment, a sample is a pair of plasma samples, in which one of the plasma pair was from activated and the other plasma pair was from non-activated blood. In one embodiment, the plasma and stimulated-plasma (in one embodiment, plasma treated with an activator comprising pokeweed mitogen as described herein) are stored "properly", which in one embodiment, is at a temperature of 4° C. (for short term storage of days), or in another embodiment, at a temperature of −20° C. or −80° C. (for long term storage of over a week), as is well known in the art. In one embodiment, the plasma may be stored for up to 2 days. In another embodiment, the plasma may be stored for up to 7 days. In another embodiment, the plasma may be stored for up to 14 days. In another embodiment, the plasma may be stored for up to 1 month. In another embodiment, the plasma may be stored for up to 6 months. In another embodiment, the plasma may be stored for up to 12 months. In another embodiment, the plasma may be stored for up to 24 months. In another embodiment, the plasma may be stored for up to 3 years. In another embodiment, the plasma may be stored for up to 5 years. In another embodiment, the plasma may be stored for up to 10 years. In another embodiment, the plasma may be stored for up to 20 years.

In another embodiment, the present invention provides a kit for the detection of hepatitis virus-specific antibodies in a subject comprising: a container for retaining a whole blood sample, wherein said container comprises a medium, said medium comprising an activator of (i) lymphocytes activated by said hepatitis virus, (ii) memory cells specific for said hepatitis virus, (iii) antibodies against said hepatitis virus, or (iv) a combination thereof. In another embodiment, the kit may additionally comprise a second container lacking said medium for retaining a whole blood sample. In another embodiment, the kit may additionally comprise an assay for the detection of hepatitis viral-specific antibodies. In another embodiment, the kit may additionally comprise instructions for use.

In another embodiment, the present invention provides an improved assay for the detection of hepatitis virus-specific antibodies in a subject comprising: a container for retaining a whole blood sample, wherein said container comprises a medium, said medium comprising an activator of (i) lymphocytes activated by said hepatitis virus, (ii) memory cells specific for said hepatitis virus, (iii) antibodies against said hepatitis virus, or (iv) a combination thereof and an assay for the detection of hepatitis viral-specific antibodies.

In another embodiment, the present invention provides a kit for the diagnosis of a hepatitis virus infection in a subject comprising: a container for retaining a whole blood sample, wherein said container comprises a medium, said medium comprising an activator of (i) lymphocytes activated by said hepatitis virus, (ii) memory cells specific for said hepatitis virus, (iii) antibodies against said hepatitis virus, or (iv) a combination thereof. In another embodiment, the kit may additionally comprise a second container lacking said medium for retaining a whole blood sample. In another embodiment, the kit may additionally comprise an assay for the detection of hepatitis viral-specific antibodies. In another embodiment, the kit may additionally comprise instructions for use.

In another embodiment, the present invention provides an improved assay for the diagnosis of a hepatitis virus infection in a subject comprising: a container for retaining a whole blood sample, wherein said container comprises a medium, said medium comprising an activator of (i) lymphocytes activated by said hepatitis virus, (ii) memory cells specific for said hepatitis virus, (iii) antibodies against said hepatitis virus, or (iv) a combination thereof and an assay for the detection of hepatitis viral-specific antibodies.

As a matter of convenience, a packaged combination of reagents in predetermined amounts with instructions for performing the diagnostic assay, e.g. kits, are also within the scope of the invention. The present invention includes a kit comprising a blood collection container containing effective concentrations of mitogens or other activators therein.

In one embodiment, the container of the kit of the present invention is for retaining whole blood samples, or in another embodiment, holding, processing, storing, maintaining or collecting a whole blood samples.

In another related aspect, the present invention's methods coupled with the present invention's kits enable the diagnostic sensitivity of the combined assay to be brought to practical levels, making it feasible for both diagnostics and for introduction into the blood banks to increase the blood safety.

Kits are also provided that are useful as a positive control for the diagnostic assays. For isolation and purification of anti-viral antibodies, the kit can contain viral proteins/antigens coupled to beads (e.g., sepharose beads or nanobeads or other nano-structures). Kits can be provided which contain the antibodies for detection and quantitation of anti-viral antibodies in vitro, e.g. in an ELISA, peptide microarray, bio-chip, or a Western blot. As with the article of manufacture, the kit comprises a container and a label or package insert on or associated with the container. The container holds a composition comprising at least one antigen recognized by the anti-viral antibodies. Additional containers may be included that contain, e.g., diluents and buffers, control antibodies. The label or package insert may provide a description of the composition as well as instructions for the intended in vitro or diagnostic use.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

In one embodiment, hepatitis infection can be detected using a diagnostic kit. In one embodiment, the diagnostic kit is one currently available. In one embodiment, a kit of the present invention may be used in conjunction with a diagnostic kit for hepatitis infection. In another embodiment, a kit of the present invention may be used in conjunction with a currently available diagnostic kit for hepatitis infection.

As used herein, the term "whole blood" means blood collected with heparin, EDTA, citrate, or any other substance that prevents coagulation and clotting. The term whole blood as used herein also includes blood collected from an animal or human with heparin, ethylenediaminetetraacetate, or any other substance that prevents coagulation and clotting. "Whole blood" can also mean blood wherein the red blood cells have been lysed while maintaining the viability of the remaining white blood cells.

The term "sample" includes samples present in an individual as well as samples obtained or derived from the individual.

In one related aspect, the term "about" as refers to plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. In one embodiment, the subject is male. In another embodiment, the subject is female. In one embodiment, the subject is a pregnant or lactating female.

In one embodiment, "and/or" as used herein refers to either component or a combination thereof.

In one embodiment, the methods of the present invention comprise the steps described. In another embodiment, the methods of the present invention consist essentially of the steps described. In another embodiment, the methods of the present invention consist of the steps described. In one embodiment, the compositions of the present invention, which in one embodiment, are kits comprise the elements described. In another embodiment, the compositions of the present invention, which in one embodiment, are kits consist essentially of the elements described. In another embodiment, the compositions of the present invention, which in one embodiment, are kits consist of the elements described.

Additional objects, advantages, and novel features of the present invention will become apparent to one ordinarily skilled in the art upon examination of the examples below. These examples are presented in order to more fully illustrate the preferred embodiments of the invention. They should in no way be construed, however, as limiting the broad scope of the invention.

EXAMPLES

Example 1

The Stimulation Index (SI), Using the Container Comprising Activators as Described Herein, for More Informed Diagnosis Based on this concept, a model was developed for distinguishing current infection from a cleared one. In this model, the levels of antibodies are measured in both the plasma (unstimulated sample) and the plasma stimulated with medium comprising an activator comprising pokeweed mitogen (stimulated sample) form the same blood sample. FIG. 1a depicts the expected change in antibody levels both type of samples over time during the course of an HCV infection.

As can be seen from this graph, the reduction in antibody levels in the plasma treated with a medium comprising an activator comprising pokeweed mitogen will happen shortly after the clearance of the HCV infection. This is due to the fact that the level of antibodies in the plasma treated with a medium comprising an activator comprising pokeweed mitogen is dependent on both the antibodies already present in the blood, and the newly produced antibodies, in culture, by HCV primed B cells. With the primed cells gone from the blood shortly after the clearance of the virus from the body, the in-vitro production will be gone too. Thus, the decrease of antibody levels in the plasma treated with a medium comprising an activator comprising pokeweed mitogen will precede the one observed in the plasma. However, if the HCV infection is a chronic one, there will always be a small set of newly primed B cells in the blood, thus maintaining the antibody levels in the plasma, and the slight increase in antibody levels in the in the plasma treated with a medium comprising an activator comprising pokeweed mitogen. Based on these two different patterns, the ratio between the antibody levels in the plasma treated with a medium comprising an activator comprising pokeweed mitogen and the antibody levels in the plasma (termed Stimulation Index=SI) will be different at the different stages of the HCV infection.

Figure 1B:
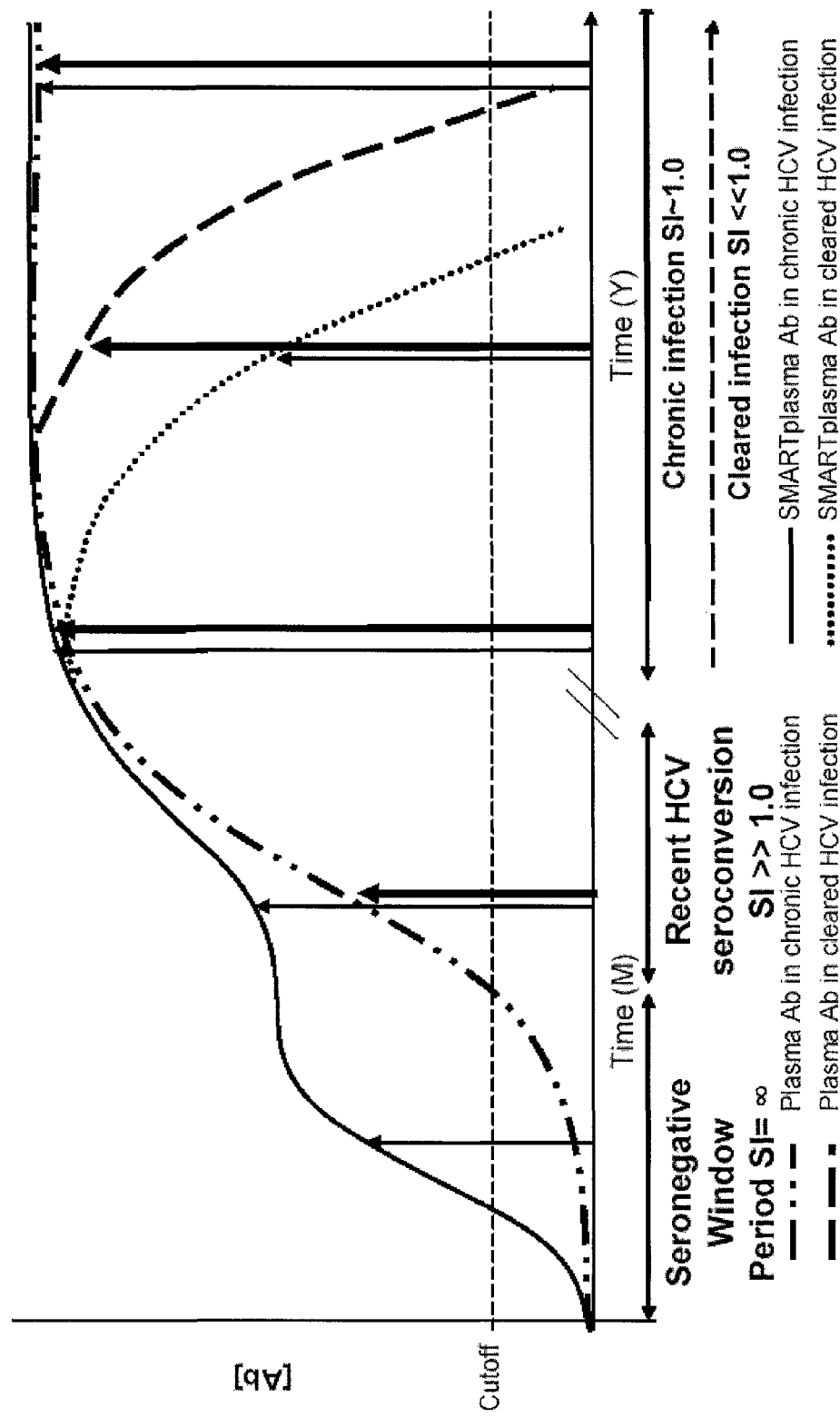

In FIG. 1b we have added arrows unto the previous graph, to depict the comparative levels of antibodies in the plasma treated with a medium comprising an activator comprising pokeweed mitogen and in the plasma (and thus the SI values). As can be seen there are 4 different possible values for the SI, and each one could serve as an indicator of a different stage in the HCV infection:

SI=∞ indicates very early infection, antibodies in the in the plasma treated with a medium comprising an activator comprising pokeweed mitogen appeared prior to seroconversion.

SI>>1.0 indicates recent seroconversion due to HCV infection. The antibody production in-vivo has not yet reached its full capacity.

SI~=1.0 indicates long term infection, not (yet) cleared.

SI<<1.0 indicates a cleared infection. While there are still high levels of antibodies in the plasma, there is no further priming of B cells, and thus no production of antibodies in-vitro.

Example 2

HCV Clinical Laboratory Results, Analyzed with the Stimulation Index (SI)

In a clinical study with the container comprising activators as described herein in Hacettepe University, Ankara, Turkey (Durmaz, N., *Turk HIV/AIDS Dergisi* 2006. 9(4): p. 112-116, incorporated herein by reference in its entirety), 500 sequential blood samples, arriving to the clinical laboratory for HCV testing, had 1.0 ml of blood transferred to the container comprising activators as described herein and the plasma treated with a medium comprising an activator comprising pokeweed mitogen was also tested using the same HCV diagnostic assay HCV Ab (Diagnostik Bioprobes, Italy). Of those 500 samples, 27 plasmas were positive in the initial antibody test. Of these, only 20 plasma treated with a medium comprising an activator comprising pokeweed mitogen samples tested positive. Further testing revealed that all the 7 plasma positive, yet none of the treated plasma negative, samples were actually false positive readings in the plasma. Thus, the diagnostic specificity of the diagnostic kit used was higher when using treated plasma as the tested sample.

A further look at the data, by calculating the Stimulation Index (SI) of the 20 seropositive samples, seems to indicate that different blood samples were taken from people at different stages of the HCV infection (Table 1).

TABLE 1

Testing for HCV using both treated plasma and plasma as the sample.

| Patient # | Standard plasma anti-HCV | Treated plasma anti-HCV | Anti-HCV immunoblot | Stimulation Index (SI) | Suggested, possible, interpretation of the SI |
|---|---|---|---|---|---|
| 9227 | 9.53 | 3.48 | − | 0.37 | |
| 9226 | 10.29 | 4.4 | − | 0.43 | |
| 5228 | 14.16 | 13.97 | + | 0.99 | Long term infection |
| 0074 | 13.35 | 7.91 | + | 0.59 | |
| 5493 | 11.15 | 8.95 | + | 0.80 | Cleared infection |
| 9137 | 9.16 | 9.16 | NA* | 1.00 | Long term infection |
| 5277 | 13.58 | 13.41 | NA* | 0.99 | Long term infection |
| 0434 | 12.97 | 13.76 | + | 1.06 | Long term infection |
| 0247 | 15.28 | 10.11 | + | 0.66 | |
| 9228 | 13.27 | 9.93 | + | 0.75 | Long term infection |
| 7815 | 11.85 | 6.05 | + | 0.51 | Cleared infection |
| 0225 | 11.82 | 15.47 | + | 1.31 | Recent infection |
| 9337 | 10.37 | 3.79 | + | 0.37 | Cleared infection |
| 8211 | 14.41 | 14.65 | + | 1.02 | Long term infection |
| 1593 | 13.24 | 15.93 | + | 1.20 | Recent infection |
| 6479 | 13.47 | 14.48 | + | 1.07 | Long term infection |
| 9087 | 12.34 | 14.34 | + | 1.16 | Long term infection |
| 1656 | 12.84 | 13.93 | + | 1.08 | Long term infection |
| 5288 | 14.09 | 14.12 | + | 1.00 | Long term infection |
| 9848 | 7.22 | 13.38 | + | 1.85 | Recent infection |
| 0452 | 12.41 | 12.14 | + | 0.98 | Long term infection |
| 5171 | 12.36 | 12.36 | + | 1.00 | Long term infection |

*Data not available.

Results are expressed as signal/cutoff.

Further research, with samples from individuals at known stages of the infection (or its clearance) are carried out to further solidify the parameters of the model proposed herein. It is important to note that in order to evaluate the container comprising activators as described herein's contribution to both HCV detection and HCV diagnosis (including staging)—the container comprising activators as described herein should be incorporated into existing, running, studies in both high risk groups and in known seropositives. This is due to the fact that the container comprising activators as described herein requires a fresh blood sample (within 24 hours, kept at room temperature), and there is no possibility of retroactively evaluating samples via freezer collections of plasma.

Figure 2:
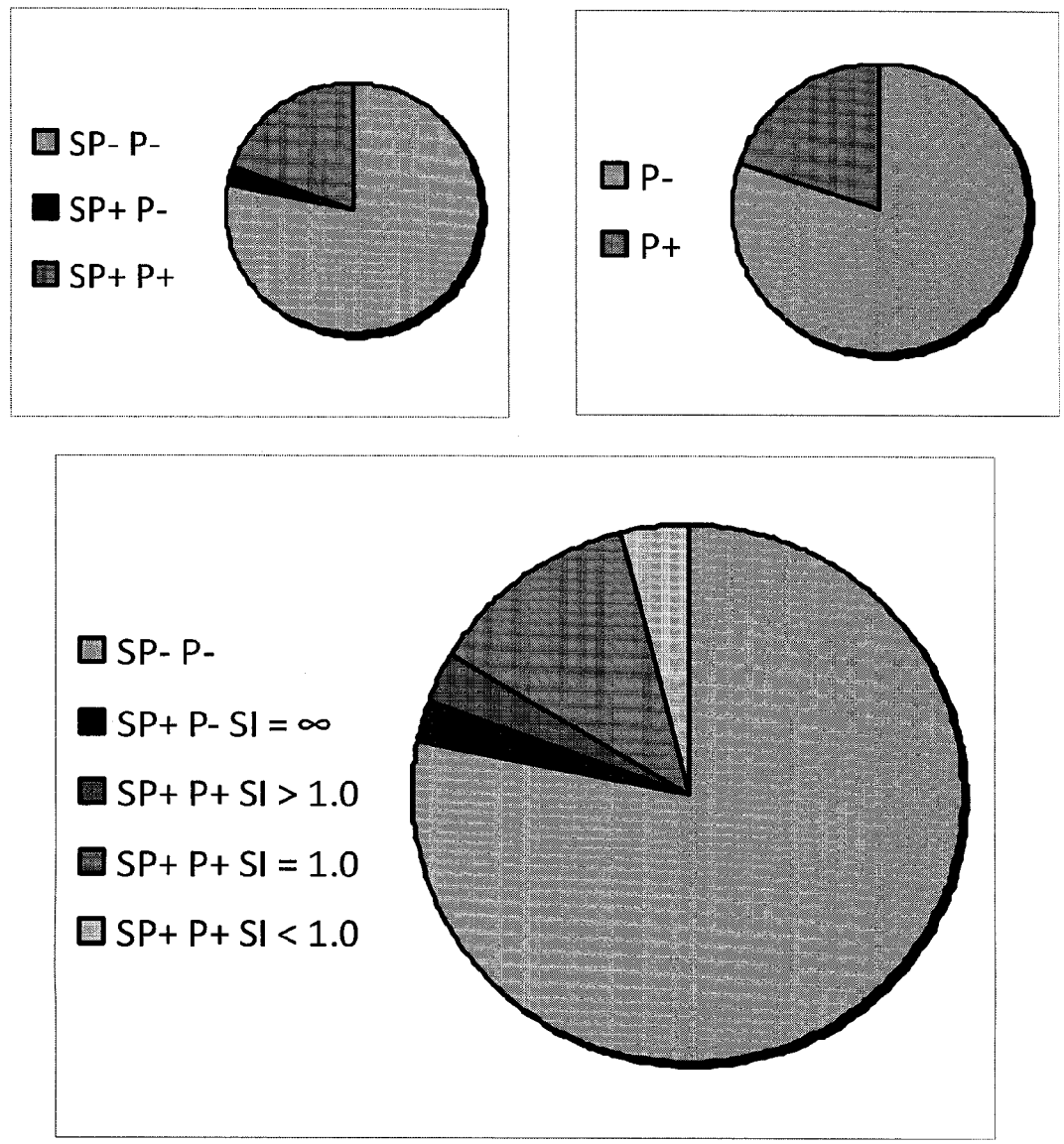
FIG. 2. The contribution of the pre-analytic step using an activator to early HCV diagnosis, and to informative Hepatitis C Virus (HCV) epidemiological data, using Enzyme ImmunoAssay (EIA) antibody assays, or any other quantitative measurement of hepatitis antibodies.

There is clearly an important role for the container comprising activators as described herein and the Stimulation Index for monitoring the HCV epidemic in different high risk populations and in suspected HCV outbreaks. If initial testing will be done using the activator-treated plasma, all infections, even prior to seroconversion, will be detectable on the currently available HCV diagnostic kits. Testing, as the second stage, the parallel plasma sample (which was kept refrigerated) of the activator-treated plasma a HCV positive ones, will enable to identify the early (seronegative) infections and to calculate the SI and thus to have a confirmed diagnosis, and an informative epidemiological picture of the HCV infections in that population (FIG. 2).

Using current serology, one can only differentiate between seropositives and seronegatives, while among the seronegatives will be all those who are not infected, and those who are infected and are still in the seronegative WP. If the activator-treated plasma is tested then the antibody positive samples will include all those who are infected and the negative antibody response in the activator-treated plasma would be a more confirmed negative diagnosis. If those testing positive on activator-treated plasma, will have also their plasma tested, then it would be possible to distinguish, among the activator-treated plasma positive samples, which ones are form individuals at the WP (those with a negative plasma results). If the plasma and the activator-treated plasma are tested using the same diagnostic ELISA assay, then the SI could be calculated. The SI information could enable the distinction of those who are recent seropositives form those which are long term infections, and, in addition, it would indicate which infections have been cleared.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A kit for the detection of hepatitis virus-specific antibodies in a subject comprising: a container for retaining a tissue sample, wherein said container comprises a medium, said medium comprising a) one or more activators of (i) lymphocytes activated by said hepatitis virus, (ii) memory cells specific for said hepatitis virus, (iii) antibodies against said hepatitis virus, or (iv) a combination thereof, and b) an anti-CD19 antibody against a B-lymphocyte membrane domain.

2. The kit according to claim 1, wherein said kit further comprises a second container lacking said medium for retaining a second tissue sample.

3. The kit according to claim 1, wherein said tissue sample is a whole blood sample.

4. The kit according to claim 1, wherein said container (a) is made of a plastic, glass, silicon, synthetic membrane, or metal, (b) is a test tube, a bottle, a well or a flask, (c) is vacuum sealed, (d) is a vacutube, or (e) comprises a polystyrene polymer, a polypropylene polymer, or a combination thereof.

5. The kit according to claim 1, wherein said container has a cap, stopper, or lid that has first and second positioning mechanism, wherein said first positioning mechanism renders the container fully closed, thereby maintaining liquid and vacuum pressure inside said container and wherein said second positioning mechanism provides ventilation to the contents of said container while preserving a sterile environment inside said container.

6. The kit according to claim 1, wherein said hepatitis virus is a hepatitis C virus (HCV).

7. The kit according to claim 1, wherein said hepatitis virus is a hepatitis B virus (HBV), a hepatitis A virus (HAV), a hepatitis D virus (HDV), or a hepatitis E virus (HEV).

8. The kit according to claim 1, wherein said medium comprises a non-carbon dioxide-dependent buffering agent.

9. The kit according to claim 8, wherein said buffering agent is HEPES ((4-(2-hydroxyethyl)-1-piperazineethane-sulfonic acid) or a phosphate-based buffering agent.

10. The kit according to claim 1, wherein said activator is pokeweed mitogen.

11. The kit according to claim 1, wherein said activator is a viral-derived peptide, lectin, bacterial endotoxin, a virus, lipid A, a cytokine, a chain of nucleotides, or a lymphokine.

12. The kit according to claim 1, wherein said lymphocytes activated by said hepatitis virus or memory cells are B-lymphocytes.

13. The kit according to claim 1, wherein said lymphocytes activated by said hepatitis virus or memory cells are T-lymphocytes.

14. The kit according to claim 1, wherein said kit is used in an assay for the detection of hepatitis viral-specific antibodies.

15. The kit according to claim 14, wherein said assay is an enzyme linked immunosorbent assay, a western blot, or an immunofluorescence assay.

16. The kit according to claim 14, wherein said kit comprises a solid phase support.

17. The kit according to claim 16, wherein said solid phase support is a nitrocellulose strip, polymer beads, synthetic beads, or a combination thereof.

18. The kit according to claim 1, further comprising a needle for drawing blood from said subject.

* * * * *